United States Patent
Yamato et al.

(10) Patent No.: US 9,909,900 B2
(45) Date of Patent: Mar. 6, 2018

(54) PEDOMETER

(71) Applicant: TDK Corporation, Minato-Ku, Tokyo (JP)

(72) Inventors: Kumiko Yamato, Kawasaki Kanagawa (JP); Kazunori Hashimoto, Konosu Saitama (JP); Akira Iguchi, Yokohama Kanagawa (JP)

(73) Assignee: TDK Corporation, Tokyo (JP)

( * ) Notice: Subject to any disclaimer, the term of this patent is extended or adjusted under 35 U.S.C. 154(b) by 721 days.

(21) Appl. No.: 14/467,441

(22) Filed: Aug. 25, 2014

(65) Prior Publication Data

US 2015/0153199 A1    Jun. 4, 2015

(30) Foreign Application Priority Data

Dec. 2, 2013    (JP) .................................. 2013-249689

(51) Int. Cl.
 *G01C 22/00*    (2006.01)
 *A61B 5/11*    (2006.01)
(52) U.S. Cl.
 CPC .......... *G01C 22/006* (2013.01); *A61B 5/1123* (2013.01)
(58) Field of Classification Search
 None
 See application file for complete search history.

(56) References Cited

U.S. PATENT DOCUMENTS

| 7,725,289 B2 | 5/2010 | Nagashima et al. | |
| 2008/0027675 A1* | 1/2008 | Noguchi | G01C 22/006 702/160 |
| 2013/0085700 A1* | 4/2013 | Modi | G01C 22/006 702/104 |
| 2013/0138394 A1* | 5/2013 | Shiga | G01C 22/006 702/160 |

FOREIGN PATENT DOCUMENTS

| EP | 1944579 A2 | 7/2008 |
| JP | 2008-084271 A | 4/2008 |
| JP | 2008-171347 A | 7/2008 |
| JP | 4957258 B2 | 6/2012 |
| JP | 2013-114486 A | 6/2013 |

OTHER PUBLICATIONS

Japanese Office Action dated May 23, 2017 in corresponding Japanese Application No. 2013-249689.

* cited by examiner

*Primary Examiner* — John Kuan
(74) *Attorney, Agent, or Firm* — White & Case LLP

(57) ABSTRACT

According to an embodiment, a pedometer includes an acceleration detecting circuit configured to detect acceleration from an output of an acceleration sensor and output an acceleration signal, a band-pass filter configured to remove, from the acceleration signal, a frequency component generated by arm swinging during walking and included in the acceleration signal, and a step counter configured to count a number of steps based on the acceleration signal outputted from the band-pass filter.

11 Claims, 4 Drawing Sheets

PEDOMETER

CROSS-REFERENCE TO RELATED APPLICATION

This application is based upon and claims the benefit of priority from the Japanese Patent Application No. 2013-249689 filed on Dec. 2, 2013; the entire contents of which are incorporated herein by reference.

FIELD

An embodiment described herein relates generally to a pedometer.

BACKGROUND

Pedometers have been widely spread. In general, the pedometer is worn on a waist or the like of a user and measures, that is, counts the number of steps from movement of the user during walking. A pedometer including an acceleration sensor can detect a change in acceleration involved in a walking motion and measure, that is, count the number of steps.

When the pedometer is worn on the waist of the user, the pedometer counts an accurate number of steps. However, when the pedometer is worn on an arm of the user, an error occurs in the measured number of steps. This is because the acceleration sensor is affected not only by acceleration corresponding to the walking motion of the user but also by acceleration corresponding to an arm swinging motion of the user.

Therefore, there has been a problem that, when the pedometer is worn on the arm and used, the pedometer cannot accurately measure the number of steps.

DETAILED DESCRIPTION

A pedometer in an embodiment includes: an acceleration detecting circuit configured to detect acceleration from an output of an acceleration sensor, which detects acceleration in one or more directions, and output an acceleration signal; a first band-pass filter configured to remove, from the acceleration signal, a frequency component generated by arm swinging during walking and included in the acceleration signal; and a first counter configured to count a number of steps based on the acceleration signal outputted from the first band-pass filter.

The embodiment is explained below with reference to the drawings.

(Configuration)

Figure 1:
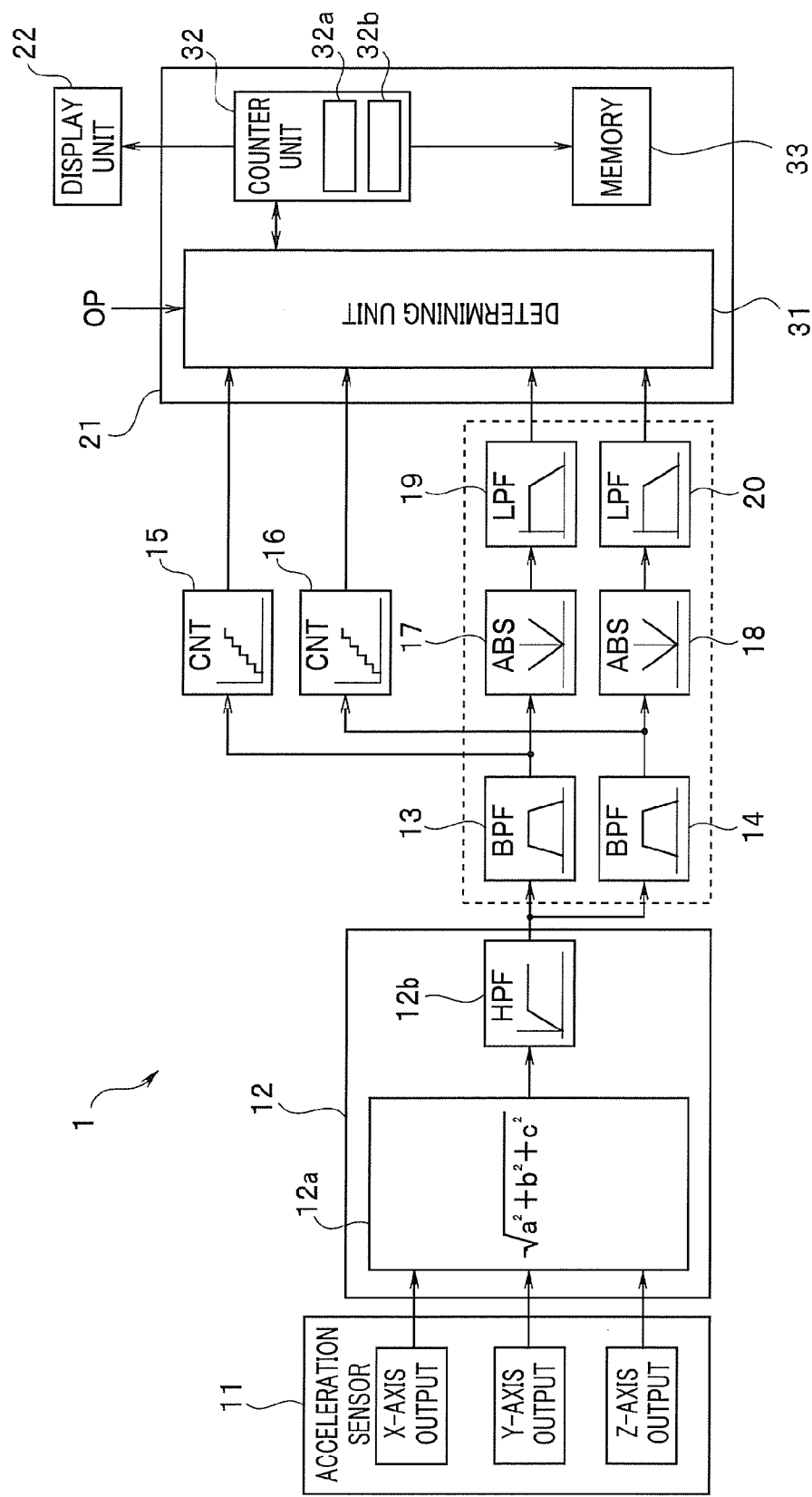
FIG. 1 is a block diagram showing a configuration of a pedometer according to an embodiment.

FIG. 1 is a block diagram showing a configuration of a pedometer according to the present embodiment. The pedometer explained below is, for example, a wristband-type pedometer attached to a wristband wound around an arm of a user.

A pedometer 1 includes an acceleration sensor 11, an acceleration detecting unit 12, two band-pass filters (BPFs) 13 and 14, two step counters 15 and 16, two absolute value circuits 17 and 18, two low-pass filters (LPFs) 19 and 20, a control unit 21, and a display unit 22.

The components other than the acceleration sensor 11 and the display unit 22 are formed in a one-chip semiconductor device as a semiconductor integrated circuit. More specifically, the acceleration detecting unit 12, the two band-pass filters 13 and 14, the two step counters 15 and 16, the two absolute value circuits 17 and 18, the two low-pass filters 19 and 20, and the control unit 21 are formed in the one-chip semiconductor device as the semiconductor integrated circuit. The control unit 21 includes a determining unit 31, a counter unit 32, and a memory 33.

Note that, in FIG. 1, an ON/OFF button for turning on and off a power supply of the pedometer 1, a reset button for resetting a count value, and the like are not shown. Operation signals OP from the buttons are inputted to the control unit 21.

The counter unit 32 includes a counter for walking 32a and a counter for running 32b. In the counter for walking 32a, the number of steps during walking of the user is counted up. In the counter for running 32b, the number of steps during running of the user is counted up.

The display unit 22 is a display device such as a liquid crystal display that displays values, that is, the numbers of steps of the counter for walking 32a and the counter for running 32b. The memory 33 stores the values, that is, the numbers of steps of the counter for walking 32a and the counter for running 32b.

The acceleration sensor 11 is a three-axis acceleration sensor including three sensors such that accelerations in three axis (X-axis, Y-axis, and Z-axis) directions orthogonal to each other can be respectively detected. The acceleration sensor 11 outputs an X-axis output, a Y-axis output, and a Z-axis output as acceleration signals concerning the respective axes.

The acceleration detecting unit 12 includes a square-root-of-sum-of-squares calculating unit 12a and a high-pass filter (HPF) 12b.

The square-root-of-sum-of-squares calculating unit 12a is a circuit that generates a signal of a square root of a sum of squares of respective outputs of the acceleration sensor 11. Since the accelerations in a plurality of directions (i.e., three directions) are used, the square-root-of-sum-of-squares calculating unit 12a that generates a signal of a square root of a sum of squares of respective outputs is used. However, a sum-of-squares calculating circuit that generates a signal of a sum of squares may be used instead of the square-root-of-sum-of-squares calculating unit 12a.

The high-pass filter 12b is an offset canceller circuit for removing gravitational acceleration from an output of the square-root-of-sum-of-squares calculating unit 12a.

Note that, although the acceleration sensor 11 is the three-axis acceleration sensor, the acceleration sensor 11 only has to be a sensor that detects acceleration in one or more directions and may be an acceleration sensor having one axis or two or more axes.

Therefore, the acceleration detecting unit 12 detects acceleration from an output of the acceleration sensor 11 that detects acceleration in one or more directions and outputs an acceleration signal.

The output of the acceleration detecting unit 12 is inputted to the two band-pass filters 13 and 14.

The band-pass filter 13 is a filter that removes a frequency component of arm swinging of the user during walking. That is, the band-pass filter 13 is a filter that removes, from the acceleration signal, a frequency component generated by arm swinging during walking and included in the acceleration signal and transmits a frequency component generated by walking included in the acceleration signal.

The band-pass filter 14 is a filter that removes a frequency component of arm swinging of the user during running (or during brisk walking). That is, the band-pass filter 14 is a filter that removes, from the acceleration signal, a frequency component generated by arm swinging during running and included in the acceleration signal and transmits a frequency component generated by running and included in the acceleration signal.

Figure 2:
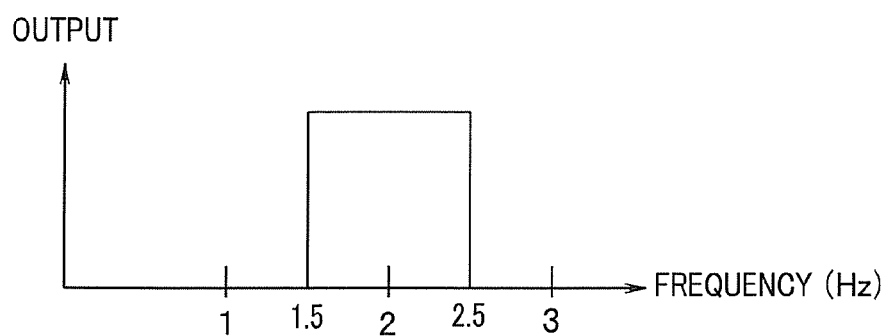
FIG. 2 is a diagram showing a filter characteristic of a band-pass filter 13 according to the embodiment.

FIG. 2 is a diagram showing a filter characteristic of the band-pass filter 13. In FIG. 2, the horizontal axis indicates a frequency and the vertical axis indicates an output of an output signal.

When a person walks, an arm is swung from a front to a back or from the back to the front per one step. In general, the user walks one to two steps per second. Therefore, the arm reciprocatingly moves once in a front-back direction per two steps.

That is, a main frequency component of an acceleration signal by walking is 1.5 Hz to 2.5 Hz. A main frequency component of an acceleration signal by arm swinging is 0.75 Hz to 1.25 Hz. The band-pass filter 13 is a filter that transmits the frequency component of 1.5 Hz to 2.5 Hz. As shown in FIG. 2, the band-pass filter 13 removes a frequency component equal to or lower than 1.5 Hz, that is, the frequency component of the arm swinging.

By using the band-pass filter 13 having the filter characteristic shown in FIG. 2, the pedometer 1 can remove an arm swinging component from an acceleration signal including information concerning accelerations of both of walking and arm swinging and select only a walking component. In the following explanation, an acceleration signal due to arm swinging is referred to as arm swinging component and acceleration signals due to the numbers of steps in walking and running are respectively referred to as a walking component and a running component.

An output of the band-pass filter 13 is inputted to a step counter (CNT) 15. The step counter 15 is a counter that counts the number of steps based on an acceleration signal outputted from the band-pass filter 13. The step counter 15 is a counter that increments the number of steps by 1 when there is an input equal to or larger than a predetermined threshold. The step counter 15 counts the number of steps based on an acceleration signal not including information concerning arm swinging in a predetermined time period (e.g., 5 seconds) and stores a value of the counted number of steps.

Figure 3:
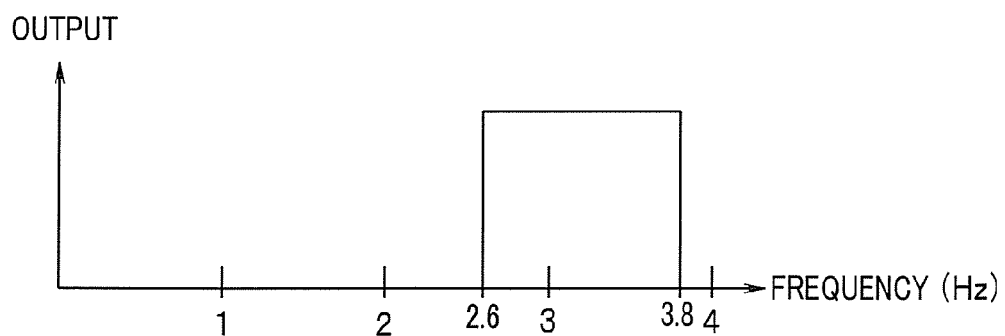
FIG. 3 is a diagram showing a filter characteristic of a band-pass filter 14 according to the embodiment.

FIG. 3 is a diagram showing a filter characteristic of the band-pass filter 14. In FIG. 3, the horizontal axis indicates a frequency and the vertical axis indicates an output of an output signal.

In general, a person runs two to four steps per second. A main frequency component of an acceleration signal by running is about 2.6 Hz to 3.8 Hz. A main frequency component of an acceleration signal by arm swinging is about 1.3 Hz to 1.9 Hz. However, there is a characteristic that, since the person folds arms during running, a component of a signal of a half of a frequency by the arm swinging is extremely small compared with the component during walking. The band-pass filter 14 is a filter that transmits a frequency component of 2.6 Hz to 3.8 Hz. As shown in FIG. 3, the band-pass filter 14 removes a frequency component lower than 2.6 Hz, that is, a frequency component of the arm swinging.

By using the band-pass filter 14 having the filter characteristic shown in FIG. 3, the pedometer 1 can remove a swinging component from an acceleration signal including information concerning accelerations of both of running and arm swinging and select only a running component.

An output of the band-pass filter 14 is inputted to the step counter (CNT) 16. The step counter 16 is a counter that counts the number of steps based on an acceleration signal outputted from the band-pass filter 14. The step counter 16 is a counter that increments the number of steps by 1 when there is an input equal to or larger than the predetermined threshold. The step counter 16 counts the number of steps based on an acceleration signal not including information concerning arm swinging in a predetermined time period (e.g., 5 seconds) and stores a value of the counted number of steps.

The count values of the step counters 15 and 16 are read out by the determining unit 31.

The outputs of the band-pass filters 13 and 14 are respectively inputted to the absolute value circuits 17 and 18. The absolute value circuits 17 and 18 are processing units that calculate and output absolute values of acceleration signals.

The outputs of the absolute value circuits 17 and 18 are respectively inputted to the low-pass filters 19 and 20. The low-pass filters 19 and 20 are processing units that output signals obtained by smoothing the acceleration signals (hereinafter referred to as acceleration energy).

Since the band-pass filter 13 outputs the acceleration signal during walking, the output of the low-pass filter 19 indicates a value proportional to energy during walking. Since the band-pass filter 14 outputs the acceleration signal during running, the output of the low-pass filter 20 indicates a value proportional to energy during running. Therefore, in FIG. 1, a part surrounded by a dotted line is an energy-by-band detecting unit. The band-pass filter 13, the absolute value circuit 17, and the low-pass filter 19 form an acceleration-energy-during-walking detecting circuit. The band-pass filter 14, the absolute value circuit 18, and the low-pass filter 20 form an acceleration-energy-during-running detecting circuit.

That is, the absolute value circuit 17 and the low-pass filter 19 form an energy detecting circuit that detects energy during walking based on the acceleration signal outputted from the band-pass filter 13. The absolute value circuit 18 and the low-pass filter 20 form an energy detecting circuit that detects energy during running based on the acceleration signal outputted from the band-pass filter 14.

According to the filter characteristics of the band-pass filters 13 and 14, when the user is walking, the low-pass filter 19 outputs the acceleration energy signal and the low-pass filter 20 does not output the acceleration energy signal. Alternatively, when the user is walking, the output of the low-pass filter 19 is larger than the output of the low-pass filter 20. According to the filter characteristics of the band-pass filters 13 and 14, when the user is running, the output of the low-pass filter 20 is larger than the output of the low-pass filter 19.

Therefore, when there is the output of the low-pass filter 19 or when the output of the low-pass filter 19 is larger than the output of the low-pass filter 20, it is possible to determine that the user is walking. When the output of the low-pass filter 20 is larger than the output of the low-pass filter 19, it is possible to determine that the user is running.

The respective outputs of the step counters 15 and 16 and the low-pass filters 19 and 20 are inputted to the determining unit 31 of the control unit 21. The acceleration energy outputted from the low-pass filters 19 and 20 is used for count control of the counter unit 32.

The determining unit 31 is a circuit that adds, based on the outputs of the low-pass filter 19 and the low-pass filter 20, the count values of the step counters 15 and 16 respectively to the count values of the two counters 32a and 32b of the counter unit 32. That is, when there is the output of the low-pass filter 19 or the output of the low-pass filter 19 is larger than the output of the low-pass filter 20, the determining unit 31 determines that the user is walking and adds the count value of the step counter 15 to the count value of the counter for walking 32a of the counter unit 32. When the output of the low-pass filter 20 is larger than the output of the low-pass filter 19, the determining unit 31 determines that the user is running and adds the count value of the step counter 16 to the count value of the counter for running 32b of the counter unit 32.

More specifically, the determining unit 31 determines, at the predetermined cycle (e.g., 5 seconds), based on the outputs of the low-pass filters 19 and 20, whether the user is walking or running. When determining that the user is walking, the determining unit 31 adds the count value of the step counter 15 in an immediately preceding period of the predetermined cycle (e.g., 5 seconds) to the count value of the counter for walking 32a. When determining based on the outputs of the low-pass filters 19 and 20 that the user is running, the determining unit 31 adds the count value of the step counter 16 in the immediately preceding period of the predetermined cycle (e.g., 5 seconds) to the count value of the counter for running 32b.

Note that, when a reset button (not shown in the figure) or the like is pressed and the operation signal OP of a reset signal is generated, the count values of the counter for walking 32a and the counter for running 32b are set to 0 (zero) to reduce the numbers of steps to 0 (zero).

As explained above, the count values of the counter for walking 32a and the counter for running 32b, that is, the numbers of steps are displayed on the display unit 22.

Each of the count values of the counter for walking 32a and the counter for running 32b is recorded in the memory 33 at each fixed time.

(Action)

When the user walks with the pedometer worn on the arm, the number of steps is counted based on acceleration of arm swinging. Therefore, the conventional pedometer sometimes counts the number of steps smaller than an actual number of steps. According to an experiment of the applicant, when the conventional pedometer was worn on the arm, the pedometer counted only the number of steps that is about 70% of an actual number of steps.

The pedometer 1 in the present embodiment includes the band-pass filters 13 and 14 that remove a frequency component of arm swinging. As shown in FIG. 2, the band-pass filter 13 transmits a frequency component of 1.5 Hz to 2.5 Hz, which is a frequency band during normal walking, and does not transmit a frequency band lower than 1.5 Hz. As shown in FIG. 3, the band-pass filter 14 transmits a frequency component of 2.6 Hz to 3.8 Hz, which is a frequency band during running, and does not transmit a frequency component lower than 2.6 Hz.

(During Walking)

When the user walks with the pedometer 1 worn on the arm, an acceleration signal detected by the acceleration detecting unit 12 is inputted to the band-pass filters 13 and 14. Then, an acceleration signal by walking obtained by excluding a signal component by arm swinging is outputted from the band-pass filter 13.

Therefore, the step counter 15 counts up with an acceleration signal equal to or larger than the predetermined threshold to thereby count the number of steps based on the acceleration signal including only a walking component.

The low-pass filter 19 outputs a signal corresponding to energy during walking.

On the other hand, since the band-pass filter 14 outputs an acceleration signal including a frequency component obtained by excluding an arm swinging signal during running, the band-pass filter 14 hardly outputs the acceleration signal during walking of the user. Therefore, an acceleration signal during walking outputted from the low-pass filter 20 is extremely small.

Based on the fact that there is the output of the low-pass filter 19 or the output of the low-pass filter 19 is larger than the output of the low-pass filter 20, the determining unit 31 determines that the user is walking. Therefore, the determining unit 31 adds a count value of the step counter 15 in a predetermined time period (e.g., immediately preceding 5 seconds) to a count value of the counter for walking 32a of the counter unit 32.

Therefore, the determining unit 31 is a selecting and outputting circuit that selects and outputs the count value of the step counter 15 in order to add the count value to the count value of the counter for walking 32a when the low-pass filter 19 forming the energy detecting circuit is outputting a value of energy or when the low-pass filter 19 is outputting a value of energy larger than an acceleration energy signal outputted by the low-pass filter 20.

(During Running)

When the user runs with the pedometer 1 worn on the arm, an acceleration signal detected by the acceleration detecting unit 12 is inputted to the band-pass filters 13 and 14. An arm swinging component is excluded from the acceleration signal. An acceleration signal including only a running component is outputted from the band-pass filter 14.

Therefore, the step counter 16 counts up with an acceleration signal equal to or larger than the predetermined threshold to thereby count the number of steps based on the acceleration signal including only the running component.

The low-pass filter 20 outputs acceleration energy during running.

On the other hand, the band-pass filter 13 is adjusted to extract a walking component and does not transmit a running component. Although an arm swinging component involved in running is outputted from the band-pass filter 13, the arm swinging component is extremely small compared with an arm swinging component outputted from the band-pass filter 14. Therefore, acceleration energy outputted from the low-pass filter 19 is extremely small compared with acceleration energy outputted from the low-pass filter 20.

Therefore, based on the fact that the output of the low-pass filter 20 is larger than the output of the low-pass filter 19, the determining unit 31 determines that the user is running. Therefore, the determining unit 31 adds a count value of the step counter 16 in the predetermined time period (e.g., immediately preceding 5 seconds) to the count value of the counter for running 32b of the counter unit 32.

Therefore, the determining unit 31 is a selecting and outputting circuit that selects and outputs the count value of the step counter 16 in order to add the count value to the count value of the counter for running 32b when the low-pass filter 20 forming the energy detecting circuit is outputting energy larger than energy outputted by the low-pass filter 19.

As explained above, when the user starts to walk with the pedometer 1 worn on the arm after resetting the pedometer 1, even if the user swings the arm, the pedometer 1 accurately counts the number of steps.

When the user starts to run with the pedometer 1 worn on the arm after resetting the pedometer 1, even if the user swings the arm, the pedometer 1 accurately counts the number of steps during running.

Figure 4:
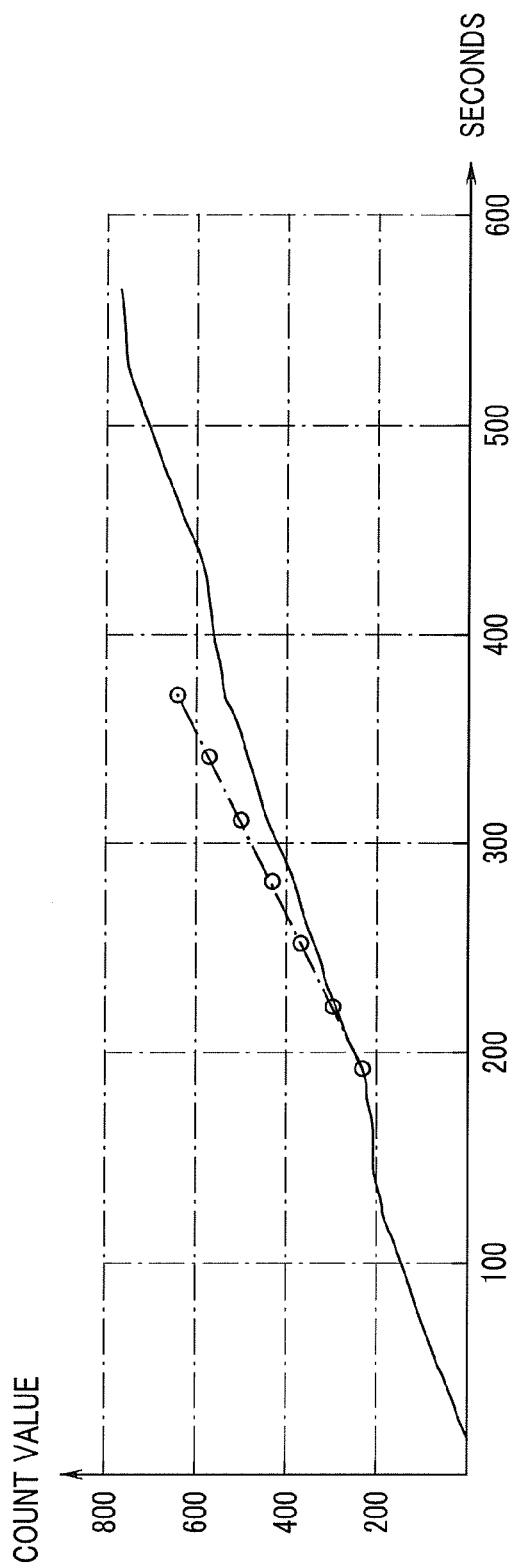
FIG. 4 is a graph in which an actual number of steps taken by a subject and the number of steps measured by a conventional pedometer when the subject walks with the conventional pedometer worn on an arm are plotted according to an elapse of time.

FIG. 4 is a graph in which an actual number of steps taken by a subject and the number of steps measured by a conventional pedometer when the subject walks with the conventional pedometer worn on an arm are plotted according to an elapse of time. In FIG. 4, the vertical axis indicates the number of steps and the horizontal axis indicates an elapsed time.

In FIG. 4, a solid line indicates a value of the number of steps measured, that is, counted by the pedometer. Circles indicate actual numbers of steps of the subject. With a certain time before elapse of 200 seconds set as a reference, an actual number of steps of the subject is plotted at every 25 seconds. According to elapse of time from the reference time, a difference between the count value of the pedometer and the actual number of steps increases.

Figure 5:
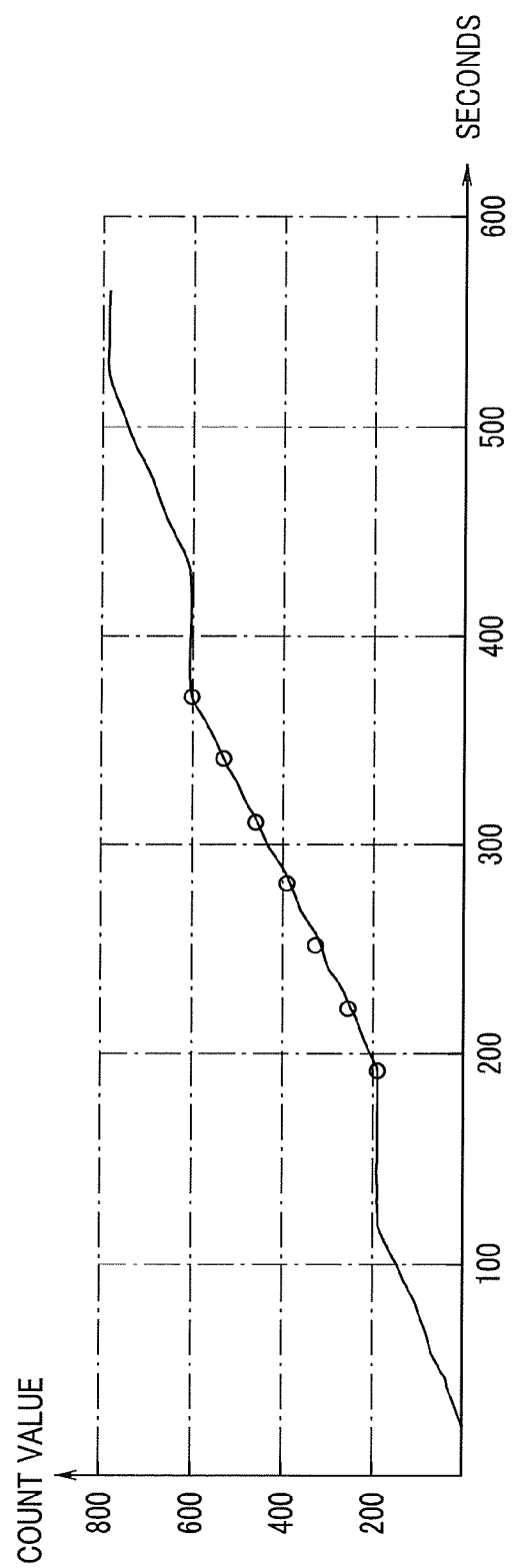
FIG. 5 is a graph in which an actual number of steps taken by the subject and the number of steps measured by the pedometer according to the embodiment when the subject walks with the pedometer according to the embodiment worn on the arm are plotted according to an elapse of time.

FIG. 5 is a graph in which an actual number of steps taken by the subject and the number of steps measured by the pedometer 1 according to the embodiment when the subject walks with the pedometer 1 according to the embodiment worn on the arm are plotted according to an elapse of time. In FIG. 5, as in FIG. 4, the vertical axis indicates the number of steps and the horizontal axis indicates an elapsed time.

In FIG. 5, as in FIG. 4, a solid line indicates a value of the number of steps measured, that is, counted by the pedometer 1. Circles indicate actual numbers of steps of the subject. With a certain time before elapse of 200 seconds set as a reference, an actual number of steps of the subject is plotted at every 25 seconds. The count value of the pedometer 1 substantially coincides with the actual number of steps. There is almost no difference between the count value and the actual number of steps.

As explained above, with the pedometer 1 in the embodiment, when the user uses the pedometer 1 with the pedometer 1 worn on the arm, the pedometer 1 can accurately measure the number of steps without being affected by arm swinging both during walking and during running.

According to the embodiment explained above, when the user repeats walking and running, the pedometer 1 determines whether the user is walking or running, automatically distinguishes the number of steps during walking and the number of steps during running, and adds the numbers of steps respectively to the counter for walking and the counter for running. Therefore, when the user repeats walking and running, the pedometer 1 internally counts the number of steps during walking and the number of steps during running separately. Therefore, the user can learn the number of steps during walking and the number of steps during running separately.

The pedometer explained above is the wristband-type pedometer attached to the wristband wound around the arm of the user. However, other forms can be adopted. For example, the pedometer may be a watch with a pedometer function in which the pedometer is incorporated in a watch. A wireless or wired communication interface may be provided in the pedometer to enable a value of the number of steps to be outputted to a smart phone, a personal computer, and the like.

Note that the pedometer in the embodiment is the pedometer that can measure the numbers of steps both during walking and during running. However, the pedometer may be a pedometer exclusive for walking not including the band-pass filter 14, the step counter 16, the absolute value circuit 18, and the low-pass filter 20 or a pedometer exclusive for running not including the band-pass filter 13, the step counter 15, the absolute value circuit 17, and the low-pass filter 19.

While certain embodiments have been described, these embodiments have been presented by way of example only, and are not intended to limit the scope of the inventions. Indeed, the novel devices described herein may be embodied in a variety of other forms; furthermore, various omissions, substitutions and changes in the form of the devices described herein may be made without departing from the spirit of the inventions. The accompanying claims and their equivalents are intended to cover such forms or modifications as would fall within the scope and spirit of the inventions.

What is claimed is:

1. A pedometer comprising:
   an acceleration detecting circuit configured to detect acceleration from an output of an acceleration sensor, which detects acceleration in one or more directions, and output an acceleration signal;
   a first band-pass filter configured to remove, from the acceleration signal, a frequency component generated by arm swinging during walking and included in the acceleration signal;
   a first counter configured to count a number of steps based on the acceleration signal outputted from the first band-pass filter;
   a second band-pass filter configured to remove, from the acceleration signal, a frequency component generated by arm swinging during running and included in the acceleration signal; and
   a second counter configured to count a number of steps based on the acceleration signal outputted from the second band-pass filter.

2. The pedometer according to claim 1, further comprising:
   a first energy detecting circuit configured to detect first energy based on the acceleration signal outputted from the first band-pass filter; and
   a selecting and outputting circuit configured to output a count value of the first counter when the first energy detecting circuit outputs a value of the first energy.

3. The pedometer according to claim 1, wherein the first band-pass filter is a filter that transmits a frequency component of 1.5 Hz to 2.5 Hz.

4. The pedometer according to claim 1, wherein the second band-pass filter is a filter that transmits a frequency component of 2.5 Hz to 4 Hz.

5. The pedometer according to claim 1, wherein the pedometer is provided in a wristband or a watch wound around an arm of a user.

6. The pedometer according to claim 1, further comprising a communication interface for outputting, by wireless or by wire, information concerning the number of steps counted by the first counter that counts the number of steps.

7. A pedometer comprising:
an acceleration detecting circuit configured to detect acceleration from an output of an acceleration sensor, which detects acceleration in one or more directions, and output an acceleration signal;
a first band-pass filter configured to remove, from the acceleration signal, a frequency component generated by arm swinging during walking and included in the acceleration signal;
a first counter configured to count a number of steps based on the acceleration signal outputted from the first band-pass filter;
a first energy detecting circuit configured to detect first energy based on the acceleration signal outputted from the first band-pass filter;
a selecting and outputting circuit configured to output a count value of the first counter when the first energy detecting circuit outputs a value of the first energy;
a second band-pass filter configured to remove, from the acceleration signal, a frequency component generated by arm swinging during running and included in the acceleration signal;
a second counter configured to count a number of steps based on the acceleration signal outputted from the second band-pass filter; and
a second energy detecting circuit configured to detect second energy based on the acceleration signal outputted from the second band-pass filter, wherein
when the second energy detecting circuit outputs a value larger than a value outputted by the first energy detecting circuit, the selection and outputting circuit selects and outputs a count value of the second counter and, when the first energy detecting circuit outputs a value larger than a value outputted by the second energy detecting circuit, the selecting and outputting circuit selects and outputs the count value of the first counter.

8. The pedometer according to claim 7, wherein the first band-pass filter is a filter that transmits a frequency component of 1.5 Hz to 2.5 Hz.

9. The pedometer according to claim 7, wherein the second band-pass filter is a filter that transmits a frequency component of 2.5 Hz to 4 Hz.

10. The pedometer according to claim 7, wherein the pedometer is provided in a wristband or a watch wound around an arm of a user.

11. The pedometer according to claim 7, further comprising a communication interface for outputting, by wireless or by wire, information concerning the number of steps counted by the first counter that counts the number of steps.

* * * * *